United States Patent [19]

Weil

[11] 4,278,771
[45] Jul. 14, 1981

[54] FLAME RETARDANT COMPOSITIONS

[75] Inventor: Edward D. Weil, Hastings-on-Hudson, N.Y.

[73] Assignee: Stauffer Chemical Company, Westport, Conn.

[21] Appl. No.: 143,652

[22] Filed: Apr. 25, 1980

Related U.S. Application Data

[62] Division of Ser. No. 49,999, Jun. 18, 1979, Pat. No. 4,242,288.

[51] Int. Cl.$^3$ .............................................. C08G 18/14
[52] U.S. Cl. ................................. 521/107; 260/45.7 P
[58] Field of Search ..................... 521/107; 260/45.7 P

[56] References Cited

U.S. PATENT DOCUMENTS

| | | | |
|---|---|---|---|
| 3,013,991 | 12/1961 | Fierce et al. | 260/929 |
| 3,210,320 | 10/1965 | Huhn et al. | 260/929 |
| 3,883,620 | 5/1975 | Turley | 521/107 |
| 3,968,187 | 7/1976 | Morgan et al. | 521/107 |
| 4,056,480 | 11/1977 | Herber | 260/929 |

FOREIGN PATENT DOCUMENTS 2302843  7/1974  Fed. Rep. of Germany ........... 260/929

Primary Examiner—Maurice J. Welsh
Attorney, Agent, or Firm—Paul J. Juettner

[57] ABSTRACT

A novel flame retardant composition is provided wherein the major component is a triphosphate ester of the formula:

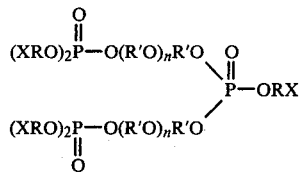

wherein R represents an alkylene radical of from 2 to about 10 carbon atoms and the halosubstituted derivatives thereof, R' represents an alkylene radical of from 2 to 3 carbon atoms, X represents a halogen of chlorine or bromine, and n is an integer of from 1 to 5. In the preferred composition, R is ethylene or propylene and R' is ethylene, X is chlorine and n is 1. The compositions are less fugitive than the prior art diphosphate compositions yet easier to prepare than low volatility phosphates presently manufactured by polycondensation.

6 Claims, No Drawings

FLAME RETARDANT COMPOSITIONS

This is a division of application Ser. No. 049,999 filed June 18, 1979 and now U.S. Pat. No. 4,242,288, issued Dec. 30, 1980.

The present invention relates to a new group of halogenated triphosphate ester compositions and their use as flame retardants.

PRIOR ART

Phosphorus flame retardant additives are well known as a class of materials. To be an effective flame retardant additive, the composition must be economical to use, compatible and non-fugitive. The term "fugitive" is used to describe a composition whose flame retarding effectiveness diminishes with aging, usually by volatilizing from the substrate. As an example, tris (2-chloroethyl) phosphate is a well known flame retardant for flexible urethane foam. This material is initially effective as a flame retardant when formulated as part of the foam forming reaction mixture. However, when the foam is subjected to aging, the flame retardancy of the foam is considerably reduced. For instance, the flame retardant volatizes from automobile upholstery material and foam and contributes to the film formed on the inside of automobile windows.

In an attempt to reduce the fugitive nature of the flame retardents, haloalkyl phosphate esters have been reacted with ethylene glycol to produce a longer chain molecule. This is disclosed in Turley U.S. Pat. Nos. 3,707,586 and 3,817,881 which disclose forming a diphosphate ester of the formula:

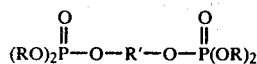

wherein R' is an alkylene radical of 1 to 8 carbon atoms and R is a haloalkyl radical.

Similar compounds are disclosed in Birum U.S. Pat. No. 3,192,242 which discloses the compounds:

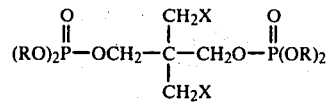

wherein R is haloalkyl and X is halogen.

A further improvement over that obtained in U.S. Pat. No. 3,707,586 is disclosed for the compounds in U.S. Pat. No. 3,976,619. Diphosphate flame retardants of the formula:

wherein R and R' represent alkylene radicals and n is 0 to 5 are prepared by reacting 2 moles of phosphorus oxyhalide with one mole of a glycol or glycol ether. This intermediate reaction product is then reacted with an oxirane compound to provide the desired diphosphate ester. The compositions of the present invention are not disclosed.

As an alternative attempt to prepare tris (2-chloroethyl) phosphate flame retardants which are less fugitive, Weil U.S. Pat. No. 3,896,187 discloses polycondensing tris (2-haloethyl) phosphate until from 0.5 to 0.9 moles of ethylene dihalide per mole of tris (2-haloethyl) phosphate are evolved. Mixed oligomers of the general formula:

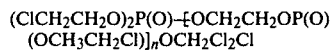

where the average n is greater than 1 are obtained. However, such polyphosphates have two faults:

(1) they contain labile cyclic impurities which require multiprocess steps to remove them as disclosed in U.S. Pat. Nos. 3,891,727; 3,959,414; 3,959,415; and 3,965,217; and (2) the process for the preparation of the original oligomer results in the formation of a toxic and wasteful organohalogen by-product.

The present invention is directed to the preparation of new flame retardant compositions with low volatility which are not required to be prepared by a polycondensation process as described above.

SUMMARY OF THE INVENTION

In accordance with the present invention, there is provided a novel flame retardant composition wherein the major component is a triphosphate ester of the formula:

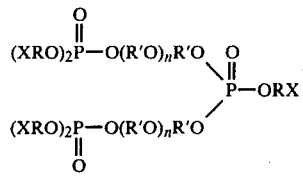

wherein R represents an alkylene radical of from 2 to about 10 carbon atoms and the halosubstituted derivatives thereof, R' represents an alkylene radical of from 2 to 3 carbon atoms, X represents a halogen of chlorine or bromine, and n is an integer of from 1 to 5. In the preferred composition R is ethylene or propylene and R' is ethylene, X is chlorine and n is 1. The invention provides compositions which are less fugitive than the prior art diphosphate compositions yet easier to prepare than the lower volatility phosphates presently manufactured by polycondensation while avoiding the multiple processing steps required to remove labile cyclic impurities inherent in the polycondensation products without forming wasteful organohoalogen by-products.

DETAILED DESCRIPTION OF THE INVENTION

The products of the invention are prepared by reacting about 3 moles of phosphorus oxyhalide with about 2 moles of polyalkylene glycol followed by reacting that intermediate reaction product with an oxirane compound.

The polyalkylene glycol used in the present invention can be represented by the formula:

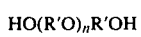

wherein R' and n are as described above. Preferably, R' represents an alkylene group of 2 carbon atoms. The symbol n is preferably 1. Illustrative of the polyalkylene glycols which can be used in the present invention are diethylene glycol, triethylene glycol, dipropylene as well as polyethylene and polypropylene glycols having repeating glycol units of five or less. Included in the term dipropylene and polypropylene glycol are all the isomeric forms thereof including the commercially available mixtures of these isomers. It is intended that the compounds of the present invention also include mixed glycol ether species prepared by using two different polyalkylene glycols in the same reaction mixture or by preparing mixed polyalkylene glycol ethers. The first provides a blend of separate compounds and the second providing a compound wherein R' groups in a molecule are mixed. Preferably, the polyalkylene glycol is diethylene or dipropylene glycol and more preferably diethylene glycol.

The oxirane compound used in the present invention can be any 1,2-alkylene oxide and halo-substituted (chlorine and bromine) 1,2-alkylene oxides having of from 2 to 10 carbon atoms. These can be illustrated by ethylene oxide, 1,2-propylene oxide, mixtures of ethylene oxide and propylene oxide, 1,2-butylene oxide, epichlorohydrin, 4,4,4-trichloro-1,2-butylene oxide and mixtures thereof. It is preferred to utilize ethylene oxide, propylene oxide and epichlorohydrin.

The phosphorus oxyhalide used in the present invention can be represented by the formula:

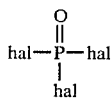

wherein the halogen can be the same or mixed members of the group of chlorine or bromine. These compounds are illustrated by phosphorus oxychloride, phosphorus oxybromide and phosphorus oxydibromidechloride. Preferably, the phosphorus oxyhalide reactant is phosphorus oxychloride.

The compositions of the present invention can be prepared by either batch or continuous process.

The phosphorus oxyhalide is preferably reacted with the glycol under slight vacuum to assist in the removal of the hydrogen halide by-product though the reaction can be conducted under atmospheric pressure or slightly elevated pressure.

The phosphorus oxyhalide and the glycol are generally reacted together at a temperature within the range of from $-10°$ C. to $80°$ C., a temperature of from $0°$ C. to $30°$ C., being preferred.

It is essential that the phosphorus oxyhalide be reacted in a mole ratio within the range of from about 2.75:2 to 3.25:2 and preferably about 3:2. The mole ratio is based on the total amount of glycol and oxyhalide added. It is not essential that the total charge of each reagent be added immediately. It is preferable that the glycol is incrementally added to the phosphorus oxyhalide.

The hydrogen halide evolved is preferably removed by vacuum though other means of purification such as sparging or the use of a refluxing inert solvent such as hexane can be useful if desired. It is preferred that the hydrogen halide be removed from the intermediate reaction mixture prior to further reaction.

The intermediate reaction mixture is reacted with an oxirane compound to give the final composition of the invention. The reaction can proceed at decreased or elevated temperatures in the presence or absence of catalysts. The use of catalysts is preferred in that reaction time is decreased and reaction temperature is lowered. Illustrative of such catalysts is titanium tetrachloride. Other catalysts are listed at Column 11 of U.S. Pat. No. 3,192,242 the subject matter of which patent is hereby incorporated by reference.

It may be desirable to conduct the oxirane reaction under heat to assure completion of the reaction. The selection of proper operating temperatures is related to the nature of the reactants, catalyst used and the quantities and can be easily determined by a skilled artisan. Temperature, within the range of $5°$ C. to $120°$ C. and preferably $30°$ C. to $90°$ C. can be employed particularly when the oxirane compound is ethylene oxide.

The oxirane compound is reacted with the intermediate reaction mixture until the reaction is substantially complete as determined by the amount of acid chloride remaining in the reaction mixture. This product can be used as is or further purified by known means such as distillation.

The compositions of the present invention are useful as flame retardants for a wide variety of natural and synthetic materials. The compositions of the invention can be effectively used as flame retardants in amounts ranging from about 0.5% by weight to about 50% and preferably from about 1% to about 25% by weight depending on the particular material and its use.

The synthetic polymers may be either linear or crosslinked polymers, and may be in the form of sheets, coatings, foams and the like. The polymers can be produced by addition or condensation.

Polymers which can be effectively flame retarded by the compositions of the present invention can be illustrated by the polymerized vinyl and vinylidene compounds, including polymeric alkenes such as polyethylene; polymerized acrylyl and alkacrylyl compounds in the form of anhydrides, esters, nitriles and amides such as alkyl acrylates and alkylmethacrylate; epoxy resins; polyesters; polyurethanes; phenolic resins; aminoplast and the like such as specifically set forth in U.S. Pat. No. 3,976,619 at Columns 6–10, the subject matter of which is hereby incorporated by reference. The polymer is preferably urethane and more preferably a flexible urethane foam.

Natural polymeric materials which may be flame retarded by the compositions of the present invention include natural rubber, cellulose esters, and similar cellulose materials.

The compositions of the invention can be employed as flame retardants for textiles such as by incorporating the composition into the spinning dope or melt of a synthetic fiber, by thermofixation or absorption into a synthetic textile such as polyester fabric or by incorporating the flame retardant composition into a surface finish, coating or backcoating. Such surface finishes, coatings or backcoating will generally contain a polymeric binder such as a styrene-butadiene elastomer latex or an acrylic latex or a thermosetting aminoplast or phenolic resin. Similar coating techniques can be used on paper or wood including incorporation of the flame retardant composition of the invention into the adhesives used for manufacturing plywood, chipboard or particle board. The compositions of the present invention can also be added as an ingredient of the polymer such as in the reactants for the formation of a flexible urethane foam or in any other manner obvious to the skilled artisan for applying the compositions. The method of addition should add on at least 0.5% by weight and preferably from about 1% to about 25% by weight based on the total weight of the polymer substrate.

The polymer formulations may also contain various conventional additives such as fillers, extenders, crosslinking agents, plasticizers, colorants, stabilizers and, in the case of foamable compositions blowing agents, catalysts, surfactants and the like as is well known to a skilled artisan.

The present invention will be more fully illustrated in the examples which follow.

EXAMPLE 1

843 grams (8 moles) of diethylene glycol was added to 1842 grams (12 moles) of phosphorus oxychloride at a temperature of 3°–8° C. over a period to five hours. The pressure during adding was maintained at 50–100 millimeters of mercury. After the addition of the glycol was complete, the reaction mixture was held at 3°–8° C. until the evolution of HCl was complete as evidenced by no further weight gain in a water filled trap on the outlet (approximately seven hours).

To a 250 grams portion of the above reaction mixture was added 1 gram of titanium tetrachloride and 1 gram of phosphorus trichloride. Ethylene oxide was passed through the reaction mixture which was maintained at 60°–65° C. until a sample of the mixture released less than 0.03 milliequivalent of acid per gram as measured by titration with 0.1 N alcoholic KOH. The reaction mixture was sparged with nitrogen to remove any excess ethylene oxide leaving a colorless water-insoluble liquid product. The product was further purified by passing the liquid through a wiped film still. The residual liquid from the still was collected as the product having the following elemental analysis for $C_{18}H_{36}Cl_5O_{14}P_3$:

Calculated: Cl, 23.7%; P, 12.4%. Found: Cl, 22.3%; P, 12.2%.

EXAMPLE 2

In like manner, the intermediate reaction product of Example 1 was reacted with propylene oxide to obtain a colorless liquid product having a viscosity of 2400 centipoises at 25° C. having the following elemental analysis for $C_{23}H_{51}Cl_5O_{14}P_3$:

Calculated: Cl, 21.6%; P, 11.32%. Found: Cl, 18.4%; P, 10.8%.

EXAMPLE 3

In like manner, the intermediate reaction product of Example 1 was reacted with epichlorohydrin to obtain a light amber product having a viscosity of 26,000 centipoises at 25° C. having the following elemental analysis for $C_{23}H_{46}Cl_{10}O_{14}P_3$:

Calculated: Cl, 35.89%; P, 9.4%. Found: Cl, 31.6%; P, 9.9%.

EXAMPLE 4

A flexible polyurethane foam was prepared utilizing the following composition:

| Reagent | Parts by Weight |
| --- | --- |
| Polyol (Niax 16-46, a commercial polypropylene glycol manufactured by Union Carbide) | 100 |
| Toluene diisocyanate | 51.09 |
| Product of Example 2 | 8.58 |
| Silicone surfactant (L-5720-Union Carbide) | 1 |
| Triethylene diamine (catalyst) | 0.30 |
| N-Ethylmorpholine (catalyst) | 0.06 |
| Stannous octoate (50% in dioctyl phthalate) (catalyst) | 0.45 |
| Water | 4.0 |

The toluene diisocyanate had an isocyanate index of 110. The foam had a cream time of 10 seconds and a rise time of 81 seconds. The density of the foam was 6.3 pounds per cubic foot and the green strength was good. Green strength is a measure of the proper gelation and easily handling characteristics. Poor green strength is demonstrated by a tacky top surface on the foam and/or a foam structure which tears easily after initial cure.

The flexible urethane foam was tested for flame retardancy using the test method described in Technical Information Bulletin 117, California Department of Consumer Affairs, Bureau of Home Furnishings, Sacramento, California. The test basically measures the average chain length of 5 specimens suspended in a burner flame. The average char length shall not exceed 6 inches and the maximum char length of any one specimen shall not exceed 8 inches. The average afterflame shall not exceed 5 seconds. The flexible urethane foam flame retarded with the compositions of the invention passed this test by providing an average chain length for 5 specimens of 3.5 inches and an average afterflame of 0.8 seconds.

Specimens of the flexible urethane foam were subjected to an accelerated dry heat aging test. The specimens were aged in a dry oven for 22 hours at 140° C. These specimens were then subjected to the flame retardancy test described above. The aged specimens also passed the test in that the average char length of the specimens was 3.9 inches and the average afterflame was 0.8 seconds.

The above described compositions when applied by padding to 100% polyester fabric and subjected to thermofixation by heating at 210° C. to 1½ minutes to achieve 4–5% add on, permitted the fabric to pass DOC-77-3-71 (children's sleepwear flammability test). A commercially available tetrakis(chloroethyl) diphosphonate did not pass this test under the same conditions of application.

What is claimed is:

1. A polymer composition containing an effective flame retardant amount of a flame retardant composition containing as its major ingredient a compound of the formula:

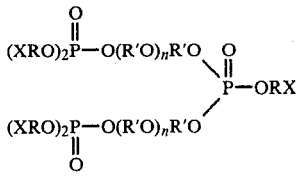

wherein R represents an alkylene radical of from 2 to about 10 carbon atoms and the halosubstituted derivatives thereof, R' represents an alkylene radical of from 2 to 3 carbon atoms, X represents a halogen of chlorine or bromine and n represents an integer of from 1 to 5.

2. The polymer composition as recited in claim 1 wherein X is chlorine.

3. The polymer composition as recited in claim 1 wherein R represents an alkylene radical of 2 or 3 carbon atoms and the halosubstituted derivatives thereof and R' represents alkylene radicals of 2 carbon atoms.

4. The polymer composition of claim 3 wherein X is chlorine, and n is 1.

5. The polymer composition as recited in claim 1 wherein said polymer is selected from the group consisting of vinyl and vinylidene polymers and copolymers; epoxy resins; urethane polymers; polymerized acrylyl and alkacrylyl esters, amides, anhydrides and nitriles; phenolic resins, aminoplasts and polyesters.

6. The polymer composition as recited in claim 5 wherein said polymer is flexible urethane foam.

* * * * *